United States Patent [19]

van Dijk

[11] Patent Number: 5,750,799

[45] Date of Patent: May 12, 1998

[54] DIMETHYL ETHER PRODUCTION AND RECOVERY FROM METHANOL

[75] Inventor: Christiaan P. van Dijk, Houston, Tex.

[73] Assignee: Starchem, Inc., Houston, Tex.

[21] Appl. No.: 404,256

[22] Filed: Mar. 15, 1995

[51] Int. Cl.⁶ .......................... C07C 41/09; C07C 41/01
[52] U.S. Cl. ............................. 568/698; 568/699
[58] Field of Search ....................... 568/698, 699

[56] References Cited

U.S. PATENT DOCUMENTS 4,665,249  5/1987  Mao et al. ........................... 585/408

*Primary Examiner*—Marianne M. Cintins
*Assistant Examiner*—Dwayne C. Jones
*Attorney, Agent, or Firm*—Pravel, Hewitt, Kimball & Krieger

[57] ABSTRACT

A process for production and recovery of dimethyl ether by dehydration of methanol which significantly reduces the distillation duties associated to the preparation of the fresh methanol feed stock and/or the recovery of unconverted methanol for use as recycle feed stock to the dimethyl ether production process while maintaining a high rate of conversion of methanol to dimethyl ether.

17 Claims, 1 Drawing Sheet

1

DIMETHYL ETHER PRODUCTION AND RECOVERY FROM METHANOL

FIELD OF THE INVENTION

This invention relates to processes for the production of dimethyl ether by dehydration of methanol, and the separation and recovery of the produced dimethyl ether from that portion of the feed methanol which remains unconverted, with recycle of the unconverted portion of methanol for further conversion into dimethyl ether.

BACKGROUND OF THE INVENTION

Dimethyl ether may be produced by the conversion of two molar quantities of methanol in contact with an acid catalyst into one molar quantity of dimethyl ether (DME) with coproduction of one molar quantity of water. The dehydration of methanol to DME is not complete and a portion of the feed methanol remains unconverted after catalyst contact and carries into the product gas composition. Heretofore, the incomplete conversion of methanol into dimethyl ether has presented no problem since the resulting methanol-dimethyl ether mixtures were produced as but an intermediate methoxy composition for further processing into other final end products.

Wherein dimethyl ether is to be recovered as the desired end product of this dehydration reaction, then for large scale production the unconverted methanol would have to be separated from the dimethyl ether product, recovered and recycled to the DME conversion reactor to complete its conversion into dimethyl ether. Separation of the DME as an isolated product from unconverted methanol and water is relatively straightforward due to the boiling point of DME of $-23°$ C. $(-9.4°$ F.) compared to that of methanol of $64.9°$ C. $(148.8°$ F.) and water of $100°$ C. $(212°$ F.). But the separation of methanol from the water by-product of the DME reaction to condition the unconverted methanol for recycle for further conversion into DME presents certain complications. With respect to conversion to DME, the methanol, whether as fresh feed stock or recycle, desirably should be relatively free of any water content since the presence of water in the feed methanol reduces the degree of methanol conversion into DME product. Even with a dry methanol, its single pass conversion to DME is equilibrium limited to about 80.8% of methanol converted. The presence of water in the feed methanol reduces this degree of methanol conversion to DME as the quantity of water in the feed methanol increases.

The product gas resulting from conversion of a dry methanol feed to DME contains 19.16 mole % of the initial methanol feed as unconverted methanol, and the unconverted methanol and water content of the produce gas are present in a relative mole fraction of their molar sum of 0.6784 water and 0.3216 methanol. Of course, any further increase in water content contributed by water contained in the feed methanol increases the mole percent of the feed methanol that goes unconverted and increases the mole fraction of water relative to unconverted methanol in the product gas. Accordingly, were DME the desired end product of the conversion process, to maximize the conversion of methanol to DME, the methanol recovery and recycling operation would require distillation processing that would separate unconverted methanol as completely as practical from the by-product water with which it is co-recovered during the DME recovery step of the process. Water carried into the product gas through the fresh methanol feed would only add to the distillation requirements needed to obtain the recycle methanol portion for the combined methanol feed.

Heretofore, the need to separate unconverted methanol from DME for recycle processing into DME has not been undertaken in a large scale conversion of methanol to DME. To the extent that prior art processes have in part converted methanol to DME in large scale, this partial conversion has been undertaken to reduce the heat exchange duties in the further processing of a methoxy compound—here both the methanol and the DME in the gas mixture containing water as steam—into other final end products, such as gasoline grade hydrocarbons. In these processes, the DME and methanol content of the product gas are but intermediate compositions used for conversion into other products and the DME-methanol product gas with its contained water is so processed without having to encounter the difficulties of the separation of the components thereof.

In commonly owned co-pending U.S. patent application Ser. No. 08/336,430, now U.S. Pat. No. 5,602,289, significant improvements in the method for production of gasoline grade hydrocarbons from methoxy compounds, such as methanol and/or DME, have been described. One embodiment of the improved methodology utilizes DME essentially free of any content of methanol and/or water. From the standpoint of making optimum use of the DME improvement therein described, it is desirable to develop a process for the production and separate recovery of DME in isolation from unconverted methanol and co-product water which accompanies the production of DME, which is practical of use from the standpoint of the capital and operational cost of the process. To this end, if such a process could be developed, it would also enable the large scale production of DME as a practical commodity chemical making it economically viable for a variety of other uses, such as an oxygenated additive for fuel stocks, for use as fuel as such and the like.

In a recent announcement at the Annual Congress of the Society of Automotive Engineers (1995) by Haldor Topsoe A/S a large scale method for manufacture of dimethyl ether has been proposed which by use of special catalyst compositions is said to produce DME directly from a synthesis gas, thus sidestepping the difficulties seen in the large scale production of DME from methanol. This proposal states that DME made from dehydration of methanol is inherently more expensive than methanol, and views the methanol dehydration process only as a stop gap measure for the small scale manufacture of DME until Haldor Topsoe's proposal for direct DME production can be put into play. Their description of conversion of methanol to DME shows a recycle of methanol as top product out of a distillation tower. Their mention of a rate of methanol conversion of around 80% corresponds to the use of an essentially water-free methanol feed to the DME reactor. To achieve such a relatively water-free methanol, both as the fresh feed stock and the methanol recycle, requires an expensive distillation of the methanol which substantially increases the cost of the DME product.

Hence there remains an unsolved desire by the art for a process for the production of DME by dehydration of methanol which is practical of application from the standpoint of cost and scale of operation.

SUMMARY OF THE INVENTION

The process of this invention utilizes methanol containing significant quantities of water, both as a fresh feed stock and/or as a recycle methanol stream, for the production of dimethyl ether (DME) which is recovered essentially free of any significant content of methanol or water. The process

3 further comprises the separation of a quantity of the water recovered in the unconverted methanol separated from the DME product in an amount sufficient to prevent water buildup in the DME process due to the methanol recycle operation. The process minimizes the distillation duties in terms of equipment costs and reflux recycle with respect to the optimum for methanol conversion to DME to provide a process that is practical for production of DME as a commodity product.

DESCRIPTION OF THE PREFERRED EMBODIMENTS

Figure 1:
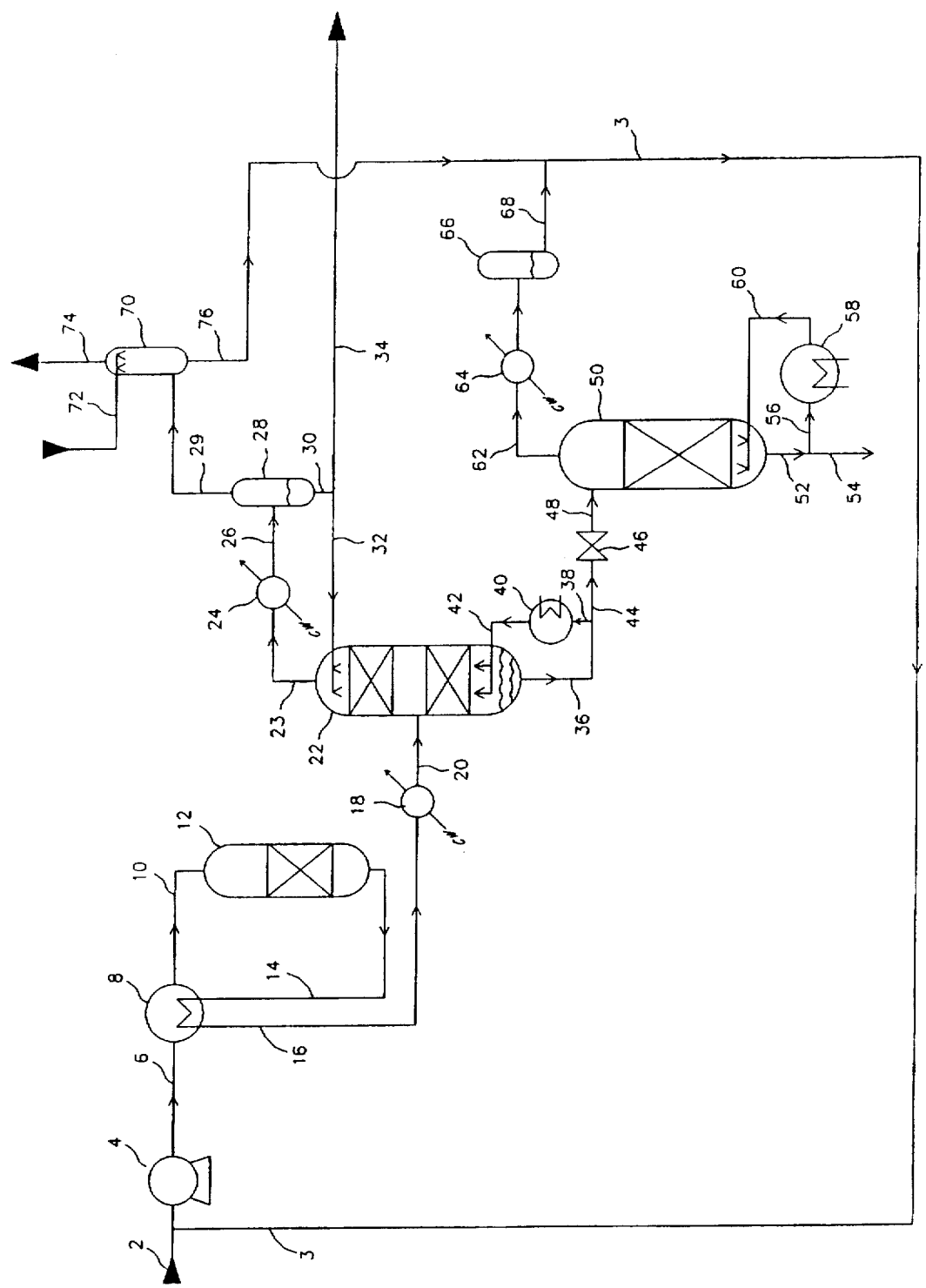
FIG. 1 illustrates a process for producing and recovering DME from the dehydration of methanol (MeOH) over an acid catalyst, with the use of a stripper for the recovery and recycle of unconverted MeOH as feed to the DME reactor and the separation and rejection from the DME process of that water contributed to the product gas from the fresh MeOH feed and as a by-product of the DME reaction.

The process of this invention utilizes methanol for production of a dimethyl ether (DME) containing reaction gas from which the dimethyl ether is recovered separately from that portion of methanol which remains unconverted and water produced as a reaction by-product or passed into the reaction product gas from the fresh methanol feed or contained in the recycled methanol. The methanol feed to the DME reactor comprises a fresh methanol feed portion and a portion of methanol recovered from the product gas and recycled back to the DME reactor.

That portion of the methanol which is the fresh methanol feed may be secured from any source. Preferably the fresh methanol feed is of a water content less than 18 weight %, more preferably less than 10 weight % water. A methanol stream of about 5 weight % water content or less may be directly produced from natural gas without the need for distillation by processes as described in U.S. Pat. Nos. 5,177,114 and 5,245,110, the descriptions of which are hereby incorporated by reference. Further, commonly owned copending U.S. patent application Ser. No. 08/336, 298 now U.S. Pat. No. 5,472,986 describes an improved process for methanol production whereby methanol of a water content of about 10 weight % or less may be produced without the need for distillation, and the description of that application is hereby incorporated by reference.

The recycle methanol portion of the methanol feed is recovered by first subjecting the DME process reaction gas to distillation treatment wherein the DME content of the product gas is separated as an overhead stream leaving the unconverted methanol and water content of the product gas to be recovered as a bottom stream. The bottom stream comprises methanol containing at least 54 weight % water. This methanol-water bottom stream is then subjected to another distillation step to produce as an overhead stream one which is more concentrated in methanol relative to water and as a bottom stream water containing no greater than 0.5 and preferably no greater than 0.05 weight % methanol. The overhead stream of this second distillation step contains at least 99% of the unconverted methanol and may be used without further distillative processing as the methanol recycle stream.

The focus for the most beneficial employment of the process of this invention is upon the operation of the second distillative step wherein the methanol-water bottom stream recovered from the DME distillation step is processed to produce a methanol recycle stream and a bottom water stream which is rejected from the DME process. Since the methanol recycle stream from this step also contains a quantity of water, this introduces water into the methanol feed to the DME reactor. To prevent water buildup from occurring in the DME production process the quantity of water rejected as a bottom stream from this step must equal that quantity of water contributed to the product gas as water from the fresh methanol feed and water by-product from the conversion of methanol to DME.

In accordance with this invention, the requisite quantity of water rejection can readily be obtained by simply distillation equipment, such as a stripper, without significant loss of methanol in the rejected water. Under appropriate selection of processing conditions for DME conversion, a stripper vessel may be employed to obtain the requisite quantity of reject water with a methanol content not exceeding about 0.05 weight % methanol. A stripper is an exceedingly simple distillation vessel which is operated without need for reflux of any portion of its overhead distillate. A dedicated stripper is a distillation vessel having no external reflux capability. The efficiency at which a dedicated stripper may be operated is essentially a function of its plate equivalency, and its reboiler duties. Still further, if desired, a refluxing distillation vessel can be employed at a low reflux ratio with a small number of theoretical plates to obtain the requisite quantity of reject water having a methanol content not exceeding about 0.05 weight % methanol. A simple overhead condenser can be employed to provide the requisite quantity of liquid reflux needed for feed back to the top of the column. A refluxing distillation column operated with a zero reflux ratio is, in effect a stripper. So employment of such a simple refluxing distillation column provides a great flexibility of the DME production process to handle fresh feed methanol having a wide range of water content.

Whether the rejection water quantity is secured by operation of a stripping vessel or a reflux distillation vessel of low reflux ratio and theoretical plate number, the overhead stream of such processing under the concepts of this invention comprises methanol with a significant content of water. This overhead stream may be used without need for further distillative processing as the methanol recycle stream for addition to the fresh methanol feed to form the combined methanol feed to the DME reactor. Though use of this overhead methanol-water stream as recycle for forming the combined methanol feed contributes water to the methanol feed, this water content of the methanol recycle only reduces the degree of methanol conversion to DME to an extent which is minor in comparison to the advantages realized from the simplified distillation duties attendant to its recovery.

With a fresh feed of methanol (MeOH) containing from about 3 to about 18 weight % water ($H_2O$), a simple stripper may be utilized to separate the MeOH-water recovered as the bottom stream from the DME recovery step into a water rejection stream and a MeOH-water recycle stream, while maintaining the single pass conversion rate of MeOH to DME on the order of a 74 to 79% conversion of methanol (91.5 to 97.7% of the theoretically possible conversion). For instance, with a fresh MeOH feed stock containing at least about 7 weight % $H_2O$, maintenance of the water balance in the DME process with a simple stripper is relatively easy to accomplish without encountering an undesirable level of MeOH loss to the rejection water while maintaining a MeOH conversion rate of at least 76%, which is about 94% of the theoretically possible rate based upon the equilibrium limitation. Greater levels of water content than about 10 weight % in the fresh MeOH feed may be accepted, which would lessen the expense of the fresh MeOH feed stock, with relatively minor effects upon the degree of MeOH conversion to DME. Hence, with a fresh feed MeOH having a water content of about 10 to about 15 weight % $H_2O$, a simple stripper may be used to provide the rejection water and MeOH-water recycle streams while maintaining the MeOH conversion level to DME at about 75% or greater (about 92.8% of theoretical).

Raw methanol having a water content in the 3 to 10 weight percent range may be directly produced without any distillate treatment by processes as described in commonly owned U.S. Pat. Nos. 5,177,114 and 5,245,119 and pending U.S. patent application Ser. No. 08/336,298, now U.S. Pat. No. 5,472,986. Use of raw MeOH as produced by these processes as the fresh MeOH feed is preferred since this allows the use of a simple stripper to obtain the rejection $H_2O$ and MeOH-$H_2O$ recycle streams needed for practice of the DME production process.

Raw MeOH produced by conventional methanol production processes, containing from about 15–18 weight % $H_2O$, may also be utilized as the fresh feed MeOH, and the necessary rejection water and MeOH-water recycle streams secured by a simple stripper, albeit the MeOH conversion to DME will be reduced to the 70–75% range (86.6 to 92.8% of theoretical).

To maintain operation of the DME process, using a wet fresh methanol feed, at a MeOH conversion rate of about 77% or greater (i.e., 95.25% of theoretical or greater) may require the use of a refluxing distillation vessel rather than a simple stripper. The reflux ratio and number of theoretical plates required are nominal. Hence a column of one theoretical plate with a top column condenser to provide liquid reflux feed to the plate will provide the needed quantity of rejection water and the MeOH-water recycle necessary to permit operation with a fresh MeOH feedstock containing 5 weight % $H_2O$ or greater. A reflux column of greater efficiency (reflux ratio of about 0.5/1) than a simple stripper would allow for operation at a 76% or greater conversion with a fresh MeO feed containing up to about 15 weight % $H_2O$.

With reference to FIG. 1, an embodiment of the process of this invention is illustrated. A source of fresh MeOH feed 2 and recycle MeOH-water 3 are combined and pressurized up to from about 10 to about 12 atmospheres absolute (ata) by compressor 4 and fed by line 6 to indirect heat exchanger 8 wherein the combined MeOH feed is heated to a temperature of from about 550° to about 650° F. by indirect heat exchange with reaction product gases fed by line 14 to heat exchanger 8. The combined MeOH feed is then passed by line 10 into reactor 12 and therein contacts an acid catalyst, such as acidic alumina, wherein a portion of the MeOH content of the combined feed is converted to DME and by-product water. The reaction product gases, comprising DME, unconverted MeOH and water, passes by line 14 through heat exchanger 8 and from there by line 16 to a chill water heat exchanger 18 wherein the product gas is cooled to from about 150° to about 200° F. and thereafter passes by line 20 to DME distillation column 22 for the separation of the DME and minor amounts of other ethers, such as methyl ethyl ether, from the unconverted MeOH and water content of the product gas.

The DME distillation column is operated at a pressure of from about 9.5 to about 11.5 ata. DME is recovered as the overhead stream 23 and passed through a chill water heat exchanger 24 and from there through line 26 to DME condenser 28. Liquid condensate 30 from condenser 28 comprises DME and other higher boiling ethers. This DME condensate passes from the condenser and is split into two streams; one portion thereof is returned by line 32 as reflux to the DME distillation column 22, the second portion is recovered as DME product and passes by the line 34 to product storage or other subsequent processing. If desired, this DME may be further distilled to separate the minor amounts of higher boiling ethers, such as methyl ethyl ether. Hence, with the process of this invention a high purity DME product can be produced without the need for a costly distillation of methanol to remove from it the minor amounts of ethanol that produce the methyl ethyl ether.

The bottom stream 36 from DME column 22 comprises MeOH and $H_2O$. This bottom stream is split, with one portion passing by line 38 through reboiler 40 wherein it is heated to from about 320° to about 480° then passes by line 42 back to the bottom section of the DME column 22. The second portion of the bottom stream passes by line 44 through valve 46 then by line 48 as feed to the top of stripper column 50 operated at about 1 ata. The bottom stream 52 from stripper 50 comprises $H_2O$ with less than 0.05 weight % MeOH. This bottom stream is split and one portion of this $H_2O$ stream is rejected from the process by line 54. The second portion of this $H_2O$ passes by line 56 to reboiler 58 where it is heated to from about 215° to about 230° F. and then returned by line 60 to the bottom section of stripper 50. The overhead stream 62 comprises MeOH and $H_2O$. This overhead stream passes to a chill water heat exchanger 64 and from there to MeOH condenser 66. The liquid MeOH condensate 68 passes from this condenser 66 by line 3 into combination with a fresh portion of MeOH feed stock supplied by line 2.

If desired, the overhead gases 29 from the DME condenser 28 may be washed with a portion of the fresh MeOH feed stock to recover any residual DME vapor from this overhead gas. In this event the overhead gases 29 are passed into scrubber 70 and a portion of the fresh MeOH feed stock supplied by line 72 is passed to scrubber 70 and after countercurrent contact with the gases, the gases are vented by line 74 and this portion of the MeOH feed is recovered by line 76 and then combined with the recycle MeOH-water stream in line 3 as illustrated (or added to the fresh MeOH feed in line 2, not illustrated).

EXAMPLES

To illustrate the point wherein it is feasible to utilize a simple stripper to process the MeOH-water stream bottoms from the DME recovery step into the rejection water and the MeOH-water recycle streams for practice of the process, a number of cases were examined wherein the fresh methanol feed varied in water content from about 1 weight % $H_2O$ up to about 18 weight % $H_2O$ and the stripper requirements were determined for the minimum molar ratio of $H_2O$:MeOH that could be obtained as a stripper overhead stream for recycle return as a portion of the total MeOH feed to the DME reactor.

Given the MeOH and $H_2O$ content of the reaction product gases that when separated from the DME would form the MeOH-$H_2O$ feed to the stripper and the theoretically possible overhead composition which this feed composition could form when processed by a stripper with an infinite number of theoretical plates, or in different words, of infinite height, expressed as the theoretical enrichment factor, an actual overhead enrichment factor for the overhead gas of at least about 96% of the theoretical enrichment factor was used for determining the overhead gas composition from the stripper. An enrichment factor is the value of the mole ratio of $H_2O$:MeOH in the feed to the stripper divided by the mole ratio of $H_2O$:MeOH in the distillate from the stripper. The results are reported in Tables IA and IB as Examples 1–11.

All values reported are based upon an equilibrium value for the reaction of MeOH to DME and $H_2O$ of 4.45. The formula weights for MeOH, $H_2O$ and DME were taken as 32, 18 and 46, respectively. The Constant-Pressure Liquid-Vapor Equilibrium Data for a methanol-water binary system as reported in Perry's Chemical Engineer's Handbook, Sixth Edition, (1984), p. 13—13 were used. Values shown for MeOH, $H_2O$ and DME are in lb-moles/hour.

TABLE IA

| | EXAMPLE NO. | | | | |
|---|---|---|---|---|---|
| | 1 | 2 | 3 | 4 | 5 |
| Fresh Feed | | | | | |
| MeOH | 100 | 100 | 100 | 100 | 100 |
| $H_2O$ | 2 | 3 | 4 | 5 | 6 |
| (wt % $H_2O$) | 1.11 | 1.66 | 2.20 | 2.74 | 3.26 |
| Recycle Feed | | | | | |
| MeOH | 27.2 | 27.49 | 27.72 | 27.94 | 28.33 |
| $H_2O$ | 14.42 | 14.84 | 14.97 | 15.09 | 15.53 |
| ($H_2O$: MeOH) | 0.53 | 0.54 | 0.54 | 0.54 | 0.55 |
| Product Gas | | | | | |
| MeOH | 27.3 | 27.59 | 27.82 | 28.04 | 28.33 |
| $H_2O$ | 66.37 | 67.79 | 68.92 | 70.04 | 71.48 |
| DME | 49.95 | 49.95 | 49.95 | 49.95 | 49.95 |
| Rejection Stream | | | | | |
| MeOH | 0.1 | 0.1 | 0.1 | 0.1 | 0.1 |
| $H_2O$ | 51.95 | 52.95 | 53.95 | 54.95 | 55.95 |
| Enrichment Factor | | | | | |
| Theoretical | 4.706 | 4.725 | 4.740 | 4.754 | 4.772 |
| Actual | 4.587 | 4.550 | 4.588 | 4.626 | 4.587 |
| (Ratio) | 0.975 | 0.961 | 0.968 | 0.973 | 0.961 |
| Percent Conversion of MeOH | | | | | |
| | 78.54 | 78.36 | 78.22 | 78.08 | 77.91 |

TABLE IB

| | EXAMPLE NO. | | | | | |
|---|---|---|---|---|---|---|
| | 6 | 7 | 8 | 9 | 10 | 11 |
| Fresh Feed | | | | | | |
| MeOH | 100 | 100 | 100 | 100 | 100 | 100 |
| $H_2O$ | 9 | 10 | 15 | 20 | 30 | 40 |
| (wt % $H_2O$) | 4.82 | 5.23 | 7.78 | 10.11 | 14.44 | 18.37 |
| Recycle Feed | | | | | | |
| MeOH | 28.91 | 29.17 | 30.28 | 31.36 | 33.47 | 35.40 |
| $H_2O$ | 15.90 | 16.34 | 17.26 | 18.19 | 20.42 | 22.40 |
| ($H_2O$: MeOH) | 0.55 | 0.56 | 0.57 | 0.58 | 0.61 | 0.63 |
| Product Gas | | | | | | |
| MeOH | 29.01 | 29.27 | 30.38 | 31.46 | 33.57 | 35.50 |
| $H_2O$ | 74.85 | 76.29 | 82.21 | 88.14 | 100.37 | 112.25 |
| DME | 49.95 | 49.95 | 49.95 | 49.95 | 49.95 | 49.95 |
| Rejection Stream | | | | | | |
| MeOH | 0.1 | 0.1 | 0.1 | 0.1 | 0.1 | 0.1 |
| $H_2O$ | 58.95 | 59.95 | 64.95 | 69.95 | 79.95 | 89.95 |
| Enrichment Factor | | | | | | |
| Theoretical | 4.812 | 4.829 | 4.894 | 4.953 | 5.061 | 5.151 |
| Actual | 4.691 | 4.654 | 4.747 | 4.830 | 4.901 | 5.019 |
| (Ratio) | 0.975 | 0.964 | 0.97 | 0.975 | 0.968 | 0.974 |
| Percent Conversion of MeOH | | | | | | |
| | 77.5 | 77.34 | 76.68 | 76.05 | 74.85 | 73.78 |

EXAMPLES 12–15

The situation of a fresh MeOH feed containing a water content of 5.32 wt % $H_2O$, or a mole ratio of MeOH:$H_2O$ of 10:1, was further examined with respect to increasing the mole ratio of $H_2O$:MeOH in the overhead from a stripper, from the 0.56 value as in Example 7 wherein the stripper would have to operate at about 96% of its theoretical maximum capacity, to values of 1.0 and 2.0 wherein a stripper would have to operate within a range no greater than 57.4% and 33.1%, respectively, of the theoretical maximum capacity of a stripper designed to operate on a MeOH-water feed that would result from these operations. Further examined was a situation of a fresh methanol feed containing 7 weight % water with a recycle MeOH feed having a mole ratio of $H_2O$:MeOH of 0.8 and a fresh MeOH feed having 15.66 weight % $H_2O$ with a recycle MeOH feed having a mole ratio of $H_2O$:MeOH of 1.0. The results are reported in Table II.

TABLE II

| | EXAMPLE NO. | | | | |
|---|---|---|---|---|---|
| | 7 | 12 | 13 | 14 | 15 |
| Fresh Feed | | | | | |
| MeOH | 100 | 100 | 100 | 100 | 100 |
| $H_2O$ | 10 | 10 | 10 | 13.38 | 30 |
| (WT % $H_2O$) | 5.33 | 5.33 | 5.33 | 7.00 | 14.44 |
| Recycle Feed | | | | | |
| MeOH | 29.17 | 32.04 | 39.36 | 31.42 | 35.98 |
| $H_2O$ | 16.34 | 32.04 | 78.72 | 25.14 | 35.98 |
| ($H_2O$:MeOH) | 0.56 | 1.0 | 2.0 | 0.8 | 1.0 |
| Product Gas | | | | | |
| MeOH | 29.27 | 32.14 | 39.46 | 31.52 | 36.08 |
| $H_2O$ | 76.29 | 91.99 | 138.67 | 88.47 | 115.93 |
| DME | 49.95 | 49.95 | 49.95 | 49.95 | 49.95 |
| Rejection Stream | | | | | |
| MeOH | 0.1 | 0.1 | 0.1 | 0.1 | 0.1 |
| $H_2O$ | 59.95 | 59.95 | 59.95 | 63.33 | 79.95 |
| Enrichment Factor | | | | | |
| Theoretical | 4.829 | 4.989 | 5.314 | 4.956 | 5.176 |
| Actual | 4.654 | 2.862 | 1.757 | 3.508 | 3.213 |
| (Ratio) | 0.964 | 0.574 | 0.331 | 0.7079 | 0.6207 |
| Percent Conversion of MeOH | | | | | |
| | 77.34 | 75.66 | 71.68 | 76.02 | 73.47 |

As may be seen by a comparison of Example 7 with Examples 12–13 as more water is accepted in the stripper overhead relative to the quantity of MeOH recovered for recycle, the requirements for the stripper in terms of its theoretical plate equivalency becomes less—meaning the cost of the stripper becomes less—although the reboiler duties of the stripper increase due to the increasing amounts of water in the top product of the stripper. In terms of the MeOH conversion rate balanced against the stripper cost, the optimum operation using a stripper lies within a mole ratio of $H_2O$:MeOH in the overhead thereof of from about 0.6 to about 2.0, preferably from about 0.7 to about 1.2 and more preferably from about 0.8 to about 1.0.

Further, as shown by the Examples, wherein one chooses to operate with a fresh MeOH feed containing about 10 to about 15 weight % $H_2O$ while maintaining a MeOH conversion rate of about 76% or greater a simple dedicated stripper could not practically be employed, however a relatively simple reflux distillation vessel could. In this event a simple distillation column operated with an overhead condenser to provide liquid reflux to the top theoretical plate at a reflux to distillate ratio as little as 0.5:1 could easily provide an overhead composition having a mole ratio of $H_2O$:MeOH of 0.25.

The invention has been described with reference to its preferred embodiments and those skilled in the art may appreciate from this description changes and modifications that may be made thereto which do not depart from the scope and spirit of the invention as described heretofore or as claimed thereafter.

I claim:

1. A process for producing dimethyl ether (DME), comprising the steps of:
    (1) contacting a feed of methanol (MeOH) comprising a fresh portion of MeOH and a recycled stream composed of MeOH and water ($H_2O$) with a dehydration catalyst to form a product gas composition composed of DME, MeOH and $H_2O$;
    (2) distilling the product gas composition to separate and recover its DME content from its MeOH and $H_2O$ content;
    (3) feeding the MeOH and $H_2O$ content from the distilling of the product gas composition to a distillation vessel to produce,
        (a) a bottom stream comprising a sum of $H_2O$ equal to that water content of the fresh portion of MeOH and that content of water produced by forming the DME content of the product gas, said bottom stream having a content of MeOH less than 0.5 weight % of the bottom stream, and
        (b) an overhead stream composed of at least 99 weight % of the MeOH content of the feed to the distillation vessel and having a mole ratio of $H_2O$:MeOH of at least 0.25, and
    (4) recycling the overhead stream from the distillation vessel into combination with a fresh portion of MeOH to form a feed of methanol for contact with the dehydration catalyst.

2. The process of claim 1, wherein said fresh feed portion of MeOH contains from about 3 to about 18 weight % water.

3. The process of claim 2, wherein at least 74% of the methanol content of the feed of methanol is converted into DME.

4. The process of claim 3, wherein at least 76% of the methanol content of the feed methanol is converted into DME.

5. The process of claim 2, wherein the overhead stream from the distillation vessel has a mole ratio of $H_2O$:MeOH of 2.0 or less.

6. The process of claim 5, wherein the distillation vessel is operated as a stripper and the overhead stream from the stripper has a mole ratio of $H_2O$:MeOH of at least 0.6.

7. The process of claim 6, wherein the overhead stream from the stripper has a mole ratio of $H_2O$:MeOH of 1.0 or less.

8. The process of claim 5, wherein at least 71.5% of the methanol content of the feed methanol is converted into DME.

9. The process of claim 7, wherein at least 75% of the methanol content of the feed methanol is converted into DME.

10. The process of claim 4, wherein said fresh feed portion of MeOH contains from about 7 weight % water.

11. The process of claim 7, wherein said fresh feed portion of MeOH contains from about 3 to about 10 weight % water.

12. The process of claim 1, further comprising the step of distilling the DME recovered from the product gas composition to separate and recover higher boiling ethers from the DME.

13. The process of claim 6, wherein the bottom stream from the stripper has a content of methanol less than 0.05 weight % of the bottom stream.

14. The process of claim 6, wherein the overhead stream of the stripper is composed of at least 99.5 wt % of the MEOH content of the feed to the stripper.

15. A process for producing dimethyl ether (DME), comprising the steps of:
    (1) contacting a feed of methanol (MeOH) comprising a fresh portion of MeOH and a recycled stream composed of MeOH and water ($H_2O$) with a dehydration catalyst to form a product gas composition composed of DME, MeOH and $H_2O$;
    (2) distilling the product gas composition to separate and recover its DME content from its MeOH and $H_2O$ content;
    (3) feeding the MeOH and $H_2O$ content from the distilling of the product gas composition to a distillation vessel to produce,
        (a) a bottom stream comprising a sum of $H_2O$ equal to that water content of the fresh portion of MeOH and that content of water produced by forming the DME content of the product gas, said bottom stream having a content of MeOH less than 0.5 weight % of the bottom stream, and
        (b) an overhead stream composed of at least 99 weight % of the MeOH content of the feed to the stripper and having a mole ratio of $H_2O$:MeOH of at least 0.6, and
    (4) recycling the overhead stream from the stripper into combination with a fresh portion of MeOH to form a feed of methanol for contact with the dehydration catalyst.

16. A process for producing dimethyl ether (DME), comprising the steps of:
    (1) contacting a feed of methanol (MeOH) comprising a fresh portion of MeOH having a water content of from about 15 to about 18 weight % and a recycled stream composed of MeOH and water ($H_2O$) with a dehydration catalyst to form a product gas composition composed of DME, MeOH and $H_2O$;
    (2) distilling the product gas composition to separate and recover its DME content from its MeOH and $H_2O$ content;
    (3) feeding the MeOH and $H_2O$ content from the distilling of the product gas composition to a refluxing distillation column operating at a reflux to distillate ratio (R/D) of 0.5 or less to produce, (a) a bottom stream comprising a sum of $H_2O$ equal to that water content of the fresh portion of MeOH and that content of water produced by forming the DME content of the product gas, said bottom stream having a content of MeOH less than 0.05 weight % of the bottom stream, and (b) an overhead stream composed of at least 99 weight % of the MeOH content of the feed to the distillation column and having a mole ratio of $H_2O$:MeOH of at least about 0.25 and (4) recycling the overhead stream from the distillation column into combination with a fresh portion of MeOH to form a feed of methanol for contact with the dehydration catalyst.

17. The process of claim 16, wherein at least 76% of the methanol content of the feed methanol is converted into DME.

* * * * *